(12) United States Patent
Hetzler et al.

(10) Patent No.: US 6,595,961 B2
(45) Date of Patent: Jul. 22, 2003

(54) STERILIZABLE TRANSFER OR STORAGE DEVICE FOR MEDICAMENTS, DRUGS AND VACCINES

(75) Inventors: Kevin George Hetzler, Sparta, NJ (US); Thea Lubrecht, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/835,446

(22) Filed: Apr. 16, 2001

(65) Prior Publication Data

US 2002/0150644 A1 Oct. 17, 2002

(51) Int. Cl.⁷ .............................. A61M 5/00
(52) U.S. Cl. ........................ 604/181; 604/187
(58) Field of Search ................. 604/181, 187, 604/192, 199, 218, 263; 128/9.19; 264/138

(56) References Cited

U.S. PATENT DOCUMENTS

| | | | |
|---|---|---|---|
| 3,919,227 A | 11/1975 | Andreades et al. | 260/85.5 R |
| 4,992,511 A | 2/1991 | Yamamoto et al. | 525/97 |
| 4,994,313 A | 2/1991 | Shimizu et al. | 428/36.7 |
| 5,187,012 A | 2/1993 | Takahashi et al. | 428/402 |
| 5,366,812 A | 11/1994 | Takahashi et al. | 428/523 |
| 5,468,803 A | 11/1995 | Takahashi et al. | 524/553 |
| 5,561,208 A | 10/1996 | Takahashi et al. | 526/281 |
| 5,637,100 A | 6/1997 | Sudo | 604/238 |
| 5,723,189 A | 3/1998 | Sudo | 428/36.9 |
| 6,007,520 A | 12/1999 | Sudo | 604/181 |
| 6,065,270 A * | 5/2000 | Reinhard et al. | 53/140 |
| 6,090,081 A * | 7/2000 | Sudo et al. | 604/218 |
| 6,164,044 A * | 12/2000 | Porfano et al. | 422/28 |
| 6,213,985 B1 * | 4/2001 | Niedospial, Jr. | 604/187 |

FOREIGN PATENT DOCUMENTS

| | | |
|---|---|---|
| EP | 0 436 372 A2 | 7/1991 |
| EP | 0 556 034 A1 | 8/1993 |
| EP | 0 709 105 A1 | 5/1996 |
| EP | 0 203 799 B1 | 8/1996 |
| EP | 0 741 989 A1 | 11/1996 |
| EP | 0 879 611 A2 | 11/1998 |
| EP | 0 920 989 A2 | 6/1999 |

OTHER PUBLICATIONS

Properties of Polymers by D. W. Van Krevelen (pp. 189–225).
CRC Handbook of Solubility Parameters and Other Cohesion Parameter, Second Edition (Allen f. M. Barton, Ph.D.) pp. 95–111 and pp. 422–429.

(List continued on next page.)

Primary Examiner—Edward K. Look
Assistant Examiner—John K Fristoe, Jr.
(74) Attorney, Agent, or Firm—David M. Fortunato

(57) ABSTRACT

A medical transfer or storage device for delivery or storage of a medicament, drug or vaccine, wherein a first component, preferably the major component, is formed of a cyclic olefin polymer, and a second component in contact with the first component is formed of a second polymer which does not chemically interact with the cyclic olefin polymeric component at elevated temperatures, including sterilization. More specifically, the relative energy distance Ra/Ro of the polymer selected for the second component relative to the cyclic olefin polymer is greater than 0.75 and the molecular weight of the second polymer is at least 5,000 to prevent adhesion of the second component to the cyclic olefin component and stress cracking at elevated temperatures. The most preferred embodiment is a syringe assembly having a cyclic olefin polymeric barrel and a resilient stopper formed of the second polymer.

13 Claims, 2 Drawing Sheets

OTHER PUBLICATIONS

Fundamental Principles of Polymeric Materials, by Stephen L. Rosen (pp. 76–81).

Article by Charles M. Hansen and Lisbeth Just Environmental Stress Cracking in Plastics.

Evaluating Environmental Stress Cracking of Medical Plastics, by Eric J. Moskala and Melanie Jones.

The Three Dimensional Solubility Parameter and Solvent Diffusion Coefficient by Charles M. Hansen.

* cited by examiner

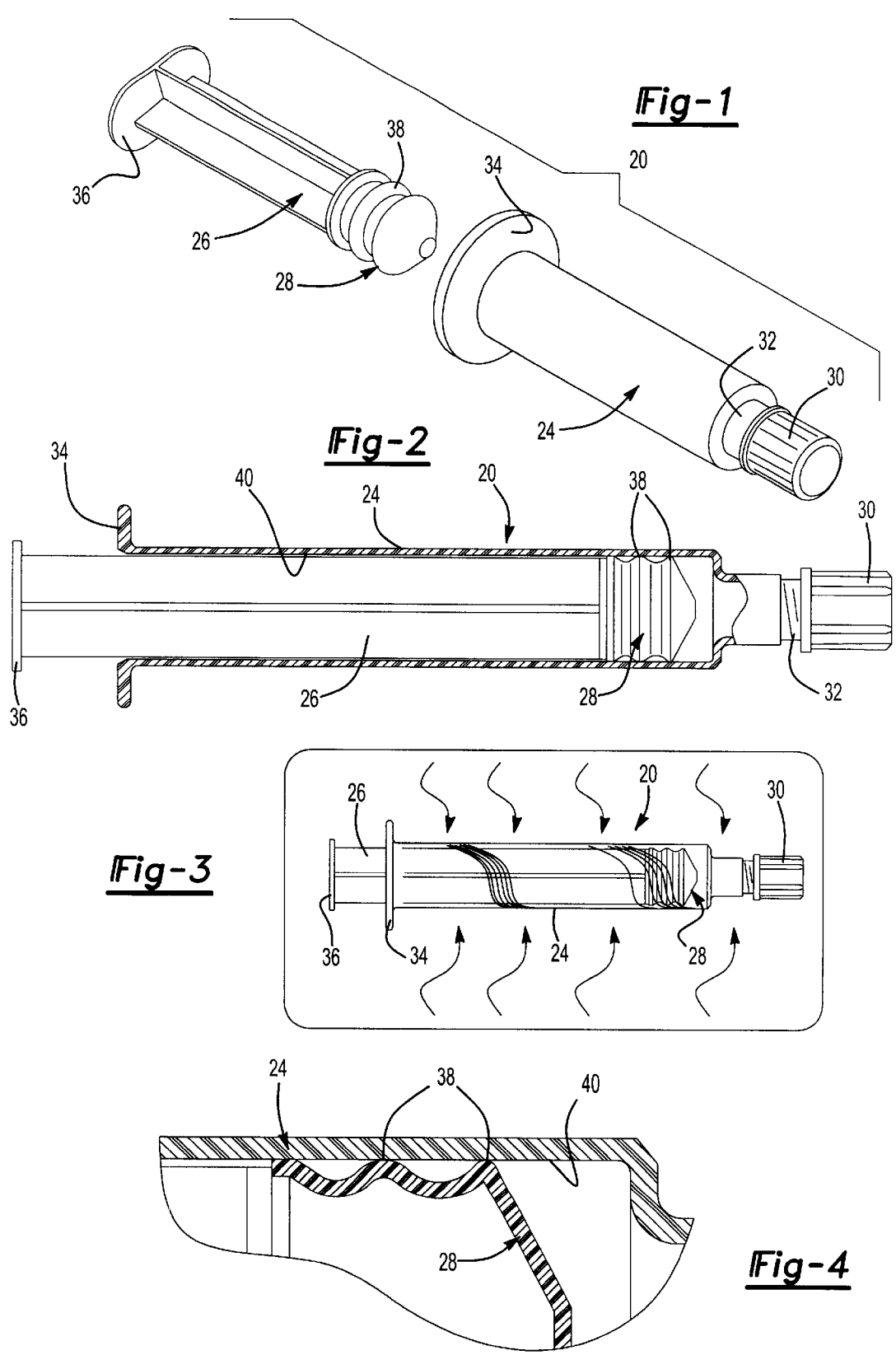

STERILIZABLE TRANSFER OR STORAGE DEVICE FOR MEDICAMENTS, DRUGS AND VACCINES

BACKGROUND OF THE INVENTION

The present invention relates to a transfer or storage device particularly, but not exclusively, for delivery or storage of a medicament, drug or vaccine, such as a syringe, transfer set, injection device or vial, wherein the major component of the delivery or storage device is preferably formed of a cyclic olefin polymer.

The development of cyclic olefin polymers has suggested the use of such polymers for manufacture of medical devices because medical devices formed of such polymers are transparent, exhibit excellent chemical resistance and may be sterilized by autoclaving or the like without damage. See European patent application EP 436,732A2. However, it has been found that medical devices, such as syringes, transfer devices and vials formed of cyclic olefin polymers are subject to stress cracking, particularly during or following sterilization, limiting the use of such polymers for medical devices. Stress cracking is defined as the crazing or cracking that may occur when a plastic under tensile stress is exposed to aggressive chemicals. The potential for environmental stress cracking is of major concern when plastics are used in medical devices because stress cracking may compromise the mechanical integrity of the device and contaminate the medicament, drug or vaccine transferred through or stored within the medical device.

Another problem with the use of cyclic olefin polymers for medical devices, such as storage or delivery devices, is adhesion of many polymers to cyclic olefin polymers following sterilization at elevated temperatures, such as autoclaving. For example, a syringe assembly includes a plunger having a stopper which withdraws fluid through the barrel tip when the stopper is withdrawn and drives fluid through the barrel tip when the stopper is advanced. Syringe stoppers are conventionally formed of a resilient synthetic rubber, such as bromo-butyl rubber, having an initial diameter greater than the internal diameter of the tubular syringe body, providing a good seal. However, when the syringe assembly is heated to the sterilization temperature of the cyclic olefin polymer and the bromo-butyl rubber stopper, the stopper firmly adheres to the cyclic olefin polymer syringe barrel making it difficult, if not impossible, to telescopically move the plunger through the tubular syringe barrel.

A similar problem exists with removable syringe tip caps or tip shields which firmly adhere or fuse to the syringe tip following heating to the sterilization temperature of the assembly. The tip caps and tip shields formed of certain polymers cannot be removed from the syringe following heating. It has also been found by the assignee of this patent application that this adhesion between various polymers and cyclic olefin polymeric transfer and storage devices following heating may also promote stress cracking. Thus, the use of cyclic olefin polymers for medical transfer and storage devices has been severely limited by these problems.

The sterilizable transfer or storage device and method of this invention solves these problems by selecting a polymer for the component in contact with the cyclic olefin polymer transfer or storage device which does not interact with the cyclic olefin polymer, even at elevated temperatures, thus permitting the use of cyclic olefin polymers for medical transfer and storage devices of the type described herein.

SUMMARY OF THE INVENTION

As set forth above, the present invention relates to sterilizable medical transfer or storage devices, such as syringes, transfer sets, vials, injection devices and the like, wherein a component, generally the major component, is formed of a cyclic olefin polymer and the device includes a second component formed of a second polymer in contact with the cyclic olefin component. More specifically, the present invention relates to the selection of the polymeric material for the second component which assures that the second component does not chemically interact with, dissolve or attack the cyclic olefin polymeric component or cause stress cracking, particularly at the elevated temperatures required for sterilization.

The polymers selected for the second member or component of the sterilizable transfer or storage device and method of this invention is based upon solubility parameters and cohesion properties explained by Charles Hansen in "*The Three Dimensional Solubility Parameter and Solvent Diffusion Coefficient*" by Charles M. Hansen, Copenhagen Danish Technical Press (1967) and the Hansen values for polymers are reported in Chapter 14 of "*The CRC Handbook and Solubility Parameters and Cohesion Parameters,*" Edited by Allan F. M. Barton (1999). Each material is defined by three points in 3D space and these three points are known as the Hansen Solubility Parameters (HSP). The Hansen Solubility Parameters may be defined as follows.

The Hansen solubility region consists of a point in 3D space defined by a non-polar dispersion interaction (Delta-D) axis, a polar or dipole interaction (Delta-P) axis and hydrogen bonding interaction (Delta-H) axis. From the location (Delta-D, Delta-P, Delta-H), a radius is projected to form a sphere which encompasses the region where liquids having HSP parameters within the inside of this sphere are generally the "attacking" the material in question, and liquids outside of the sphere are generally not attacking the material in question (See also "*Environmental Stress Cracking In Plastics,*" Hansen and Just, Pharmaceutical and Medical Packaging (1999), Vol. 9, 7.1 to 7.7, ISBN 87-89753-26-7. Hansen also noted that higher stress/temperature levels will enlarge the sphere (increase the radius) as well as the size and shape of the liquid molecules. Generally, the larger the molecule, the harder it is for the molecule to attack the material in question. Thus, as discussed further below, the molecular weights of the components are also important to prevent interaction. The assignee of this application has noted material interactions under ambient conditions, but material interaction is found more frequently at elevated temperatures, such as during autoclaving and annealing. As set forth above, however, the problems associated with material interaction between cyclic olefin polymers and the polymers conventionally used for components of medical devices has severely limited the use of cyclic olefin polymers in medical transfer and storage devices.

The distance between the HSP coordinate of polymer A to HSP coordinates of another material (liquid or Polymer B) is defined as Ra. The radius of the Polymer A sphere is defined as Ro. Ra/Ro is now defined by Hansen as the Relative Energy Distance (RED). Hansen reports that if Ra/Ro is less than 1, the two materials may stress crack or dissolve each other. If Ra/Ro is greater than or equal to 1, the materials do not have an affinity to one another under standard conditions. Ro is determined through experimentation described by Hansen, and the 3D distance, Ra, is defined by the equation:

$$(Ra)^2 = 4(\text{Delta-}D_1 - \text{Delta-}D_2)^2 + (\text{Delta-}P_1 - \text{Delta-}P_2)^2 + (\text{Delta-}H_1 - \text{Delta-}H_2)^2$$

1=polymer
2=liquid ($2^{nd}$ solid in this disclosure)
and
RED=Relative Energy Distance=Ra/Ro Ra/Ro is inside the polymer sphere if it is less than 1
Ra/Ro is on the surface of the sphere if it is 1
Ra/Ro is outside the polymer sphere if it is greater than 1.
For Ticona Topas® cyclic olefin copolymers, the Hansen Solubility Parameters have been reported by Hansen to be:
Delta-D=18.0, Delta-P=3.0 and Delta-H=2.0 and Ro=5.0
For Ticona Topas, a cyclic olefin, which has seen cracking the Hansen Solubility Parameters have been reported by Hansen to be:
Delta-D=17.3, Delta-P=3.1 and Delta-H=2.1 and Ro=6.4.
The stress cracked Ticona resin has a bigger sphere, more easily attacked than non-stress cracked Topas material.

Thus, the larger the Hansen solubility difference between two polymers, the less likely the polymers will destructively interact. Experimentation by the applicant has shown that this difference is particularly important in the use of cyclic olefin polymers in medical devices which must be sterilized before use. As stated above, Hansen has also found that an increase in temperature will enlarge the sphere of interaction. For example, it has been found by the applicant that a syringe stopper will have a lower breakout force and a lower sustaining force when the relative energy distance Ra/Ro is increased to greater than 0.75 or most preferably equal to or greater than one; which prevents adhesion of the plunger stopper to a cyclic olefin polymer barrel and reduced stress cracking of the barrel at elevated temperatures, such as the sterilization temperature. For example, it has been found by the applicant that a bromo-butyl rubber stopper in a syringe formed of a cyclic olefin polymer has a breakloose force of approximately 4.5 kg., whereas a styrene-butadiene rubber stopper has a breakout force of only approximately 1.0 kg. The applicant has determined that the relative energy distance Ra/Ro of butyl rubber relative to a conventional cyclic olefin polymer is 0.3, whereas the relative energy distance Ra/Ro of styrene-butadiene rubber compared to the cyclic olefin polymer is about 1.0. Further, it has been found that a bromo-butyl rubber stopper in a cyclic olefin polymer syringe barrel will fuse to the barrel following autoclaving, whereas a styrene-butadiene rubber stopper in a cyclic olefin polymer syringe barrel will not be adversely affected by autoclaving. Further experimentation has shown that where the relative energy distance Ra/Ro of the polymer used for the plunger relative to a syringe barrel formed of a cyclic olefin polymer is greater than about 0.75, the plunger will not adversely adhere to the barrel or cause stress cracking of the barrel.

The sterilizable storage device of this invention thus comprises a first member, preferably a major component, such as a syringe barrel, transfer set, vial, cartridge or the like formed from a cyclic olefin polymer and a second member or component, such as a syringe stopper, tip cap or tip shield formed of a second polymer or a composite or laminate or coating wherein the interface layer is formed of the second polymer, wherein the relative energy distance Ra/Ro of the second polymer relative to the cyclic olefin polymer is greater than 0.75 or more preferably equal to or greater than one which prevents adhesion of the second component to the first component and stress cracking. A high molecular weight/molar volume of the non-cycling olefin polymer also prevents the non-cyclic olefin polymer from attacking the cyclic olefin. In the most preferred embodiment, the cyclic olefin component has a molecular weight of at least 20,000 and the non-cyclic olefin component has a molecular weight of at least 5,000 or more preferably greater than 7,500.

A preferred embodiment of this invention is a syringe barrel formed of a cyclic olefin polymer and a plunger stopper formed of a second polymer which has the requisite relative energy distance. Another preferred embodiment is a syringe barrel formed of a cyclic olefin polymer and a tip cap or tip shield formed of a second polymer, as described. As set forth above, the syringe stopper, for example, may be formed of a styrene-butadiene or a fluorocarbon polymer. However, it is believed that other polymers, polymer/compositions would be suitable for the second polymer provided the relative energy distance Ra/Ro of the second polymer relative to the cyclic olefin polymer is greater than 0.75. In the most preferred embodiment, the relative energy distance Ra/Ro of the second polymer is equal to or greater than 0.8 or most preferably greater than 1.

Thus, the most preferred method of making a sterilized syringe assembly, for example, comprises the steps of forming a syringe body from a cyclic olefin polymer, forming a plunger stopper from a second polymer, wherein the relative energy distance Ra/Ro of said second polymer relative to said cyclic olefin polymer of the syringe body is greater than 0.75. The plunger is then telescopically received in the tubular syringe barrel with the plunger stopper in contact with the syringe barrel. Finally, the syringe barrel and plunger stopper are heated to the sterilization temperature of the syringe barrel and plunger stopper. The method of making a sterilizable syringe assembly may also include forming a tip cap or tip shield from a third polymer, which may be identical to or different from the second polymer, and wherein the relative energy distance Ra/Ro of the third polymer relative to the cyclic olefin polymer is greater than 0.75 and assembling the tip cap or tip shield on the syringe body before heating.

Thus, the sterilizable transfer or storage device and method of this invention solves the problems associated with using a cyclic olefin polymer for such medical devices and permits sterilization of the assembly without stress cracking or adhesion of the components. Other advantages and meritorious features of this invention will be more fully understood from the following description of the preferred embodiments, the appended claims and the drawings, a brief description of which follows.

BRIEF DESCRIPTION OF THE DRAWINGS

FIG. 1 is an exploded view of a syringe assembly illustrating one preferred embodiment of this invention;

FIG. 2 is a side cross-sectional view of the syringe assembly shown in FIG. 1 following assembly;

FIG. 3 is a side cross-sectional view of the syringe assembly shown in FIG. 2 during sterilization;

FIG. 4 is an enlarged partial side cross-sectional view of FIG. 2; and

DESCRIPTION OF THE PREFERRED EMBODIMENTS

Figure 5:
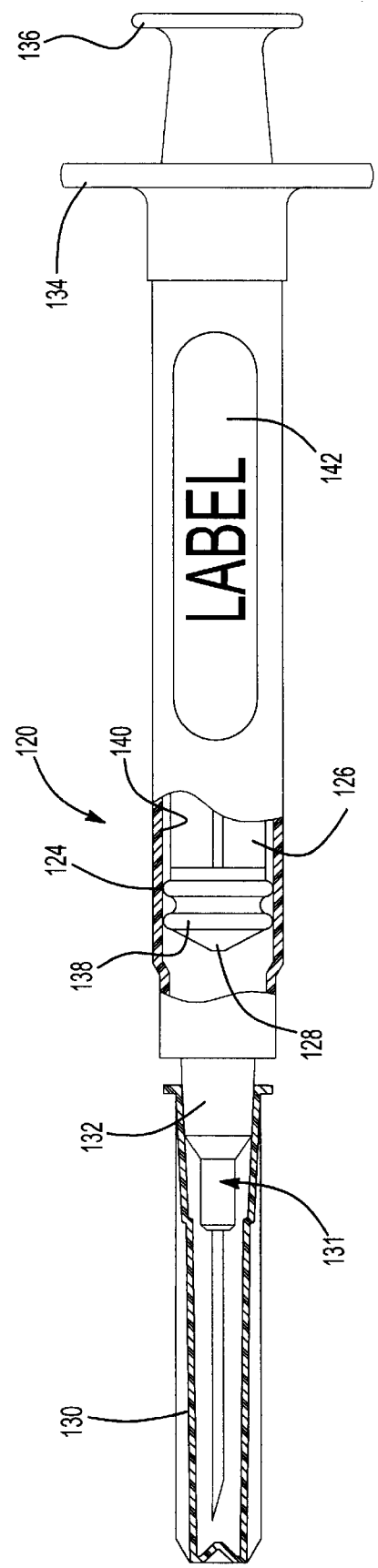
FIG. 5 is a side cross-sectional view of another embodiment of a syringe assembly of this invention.

As described above, this invention relates to a sterilizable medical transfer or storage device for delivery or storage of a medicament, drug or vaccine, wherein a component of the device, generally the major component, is formed of a cyclic olefin polymer. As used herein, the term "cyclic olefin polymer" is intended to broadly cover the family of cyclic olefin polymers/copolymers, including bridged cyclic olefin polymers as disclosed, for example, in the patents of Nippon Zeon Co., Ltd., including U.S. Pat. No. 5,561,208 and European patent publication EP 920 989 A2. As will be understood, however, cyclic olefin polymers are available from a variety of sources including Dow Chemical Company which makes a polycyclohexylenethylene and Ticon, a division of Celanese AG (formerly Hoechst Technical Polymers), which makes a cycloolefin copolymer under the tradename "Topas". A suitable cyclic olefin polymer for the sterilizable transfer or storage device and method of this invention is available from Nippon Zeon Co., Ltd. under the trade name Zeonex™. As set forth above, cyclic olefin polymers have characteristics and properties which strongly recommend the use of such polymers for medical applications, including excellent transparency, chemical resistance, etc. However, such use has been inhibited by chemical interaction resulting in adhesion, dissolving or fusion with other polymers typically used for components of such medical devices and stress cracking, particularly at the elevated temperatures required for sterilization, which is generally between 120 to 125 C for about 50 minutes.

The sterilizable transfer or storage device and method of this invention solves these problems by selection of the polymer for the components of the device in contact with the cyclic olefin polymeric component which avoids chemical interaction with the cyclic olefin polymeric component based upon the Hansen relative energy distance Ra/Ro discussed in detail above. More specifically, the sterilizable transfer or storage device of this invention comprises a first member formed of a cyclic olefin polymer, which is preferably the major component of the device such as a syringe barrel, transfer set, vial or the like. The transfer or storage device further includes a second member or component in contact with the first member formed of a second polymer, wherein the relative energy distance Ra/Ro of the second polymer relative to the cyclic olefin polymer is at least 0.75 to prevent adhesion of the second member to the first member and stress cracking of the cyclic olefin polymer member at elevated temperatures, including sterilization, annealing, etc. Although the sterilizable transfer or storage device and method of this invention has several applications, particularly in regard to medical devices, the invention will now be described in regard to a syringe for delivery or storage of a medicament, drug or vaccine, as follows.

FIGS. 1 to 4 illustrate one embodiment of a syringe assembly 20 suitable for the sterilizable storage or delivery device and method of this invention. The syringe assembly 20 shown in FIGS. 1 to 4 includes a generally tubular barrel 24 and a plunger 26 having a resilient stopper 28 telescopically received in the generally tubular barrel 24 as best shown in FIG. 2. In this embodiment, the syringe assembly 20 further includes a tip cap 30 threadably received on the reduced diameter tip portion 32 of the barrel. The syringe barrel 24 may also include an integral flange portion 34, which provides a finger grip, and the plunger may also include a flange 36 which assists the healthcare worker to withdraw or advance the plunger 26 in the barrel 24. In this embodiment of the syringe assembly 20, the resilient stopper 28 includes a plurality of radial rib portions 38 which contact the internal surface 40 of the barrel 24, providing a seal during withdrawal and advance of the plunger 26 in the barrel 24.

As will be understood by those skilled in this art, a syringe assembly of this type may be utilized for storage and delivery of medicaments, drugs or vaccines. That is, the syringe may be prefilled to store a medicament, drug or vaccine and the syringe assembly may then be utilized to transfer a medicament, drug or vaccine to a patient. The tip cap 30 may be threadably removed from the barrel tip 32 and a needle cannula (not shown) may be threadably assembled on the tip 32 for delivery of a medicament, drug or vaccine to a patient by advancing the plunger 26. In the preferred embodiments of this invention, the barrel 24 is formed from a cyclic olefin polymer and the polymer used to form the stopper 28 and tip cap 30 is selected to avoid a chemical interaction between the polymers selected for these components and the cyclic olefin polymeric barrel 24. More specifically, the relative energy distance Ra/Ro of the polymers selected for the stopper 28 and tip cap 30 relative to the cyclic olefin polymer of the barrel 24 is greater than 0.75 or more preferably equal to or greater than 1 to prevent adhesion or fusion of the stopper 28 and the tip cap 30 to the barrel 24 and stress cracking of the barrel at elevated temperatures including sterilization. Experimentation has shown that where the relative energy distance Ra/Ro is less than about 0.75, the portions of the stopper 28 and the tip cap 30 in contact with the barrel 24 will fuse to the barrel during autoclaving. As shown in FIG. 4 and described above, the stopper 28 includes a plurality of radial rib portions 38 which must resiliently contact the internal surface 40 of the barrel 24 to provide a seal. During autoclaving, these rib portions 38 will fuse to the internal surface 40 of the barrel where the relative energy distance Ra/Ro of the polymer selected for the plunger relative to the cyclic olefin polymer of the barrel is less than about 0.75 and result in stress cracking of the barrel. Similarly, the tip cap 30 will fuse to the tip 32 during autoclaving where the polymers selected for the tip cap 30 relative to the cyclic olefin polymer barrel 24 is less than about 0.75. In the most preferred embodiments, this ratio is greater than 1.

Thus, polymers including butyl rubber, chlorobutyl rubber, nitrile butadiene, isobutylene/isoprene and isoprene elastomers having a relative energy distance Ra/Ro of about 0.5 will fuse to a cyclic olefin polymer barrel at elevated temperatures including autoclaving, whereas styrene-butadiene and fluorocarbon polymers including Teflon® having a relative energy distance Ra/Ro of about 1 or greater will not chemically interact with a cyclic olefin polymer barrel and are therefore acceptable as the second component of the syringe assembly 20, such as the stopper 28 and the tip cap 30. As will be understood, the second component may be formed of any suitable material provided the interface of the second component, which may be formed by coating, lamination, etc. is formed of a polymer as described herein. Although fluorocarbon polymers are acceptable, such polymers are relatively expensive and are therefore not included in the most preferred polymers for the second component.

The method of making a sterilizable syringe assembly of this invention therefore includes forming a generally tubular syringe barrel 24 from a cyclic olefin polymer; forming a plunger stopper 28 from a second polymer, wherein the relative energy distance Ra/Ro of the second polymer to the cyclic olefin polymer of the syringe barrel is greater than 0.75 as shown in FIG. 1; telescopically receiving the plunger stopper 28 in the generally tubular barrel 24 as shown in FIG. 2 with the plunger stopper 28 in contact with an inside surface 40 of the generally tubular barrel as shown in FIG. 4; and then heating the syringe barrel and plunger stopper to the sterilization temperature of the barrel and plunger stopper as shown in FIG. 3. Similarly, where the syringe assembly 20 includes a tip cap as shown at 30, the method further includes forming the tip cap 30 of a third polymer, which may be identical to or different from the polymer selected for the stopper 28, wherein the relative energy distance Ra/Ro of the polymer selected for the tip cap relative to the cyclic olefin polymer of the barrel 24 is greater than 0.75, assembling the tip cap on the syringe barrel as described and then heating the assembly to the sterilization temperature of the assembly.

FIG. 5 illustrates an alternative embodiment of a syringe assembly 120 which includes a generally tubular barrel 124, a plunger 126 having a stopper 128 and a tip shield 130 which is received on the reduced diameter tip portion 132 of the barrel. The tip shield 130 encloses a needle cannula assembly 131 secured to the end of the reduced diameter barrel portion 132, as shown. As described above, the barrel 124 may also include a finger grip 134 and the plunger may include a flange 136. The stopper 128 may also include a plurality of radial rib portions 138 which sealingly engage the internal surface 140 of the barrel 124. The syringe assembly 120 further includes a label 142 which is affixed to the external surface of the barrel 124. Thus, in this embodiment, the plunger stopper 128, tip shield 130 and label 142 contact the barrel 124, which is preferably formed of a cyclic olefin polymer as described above. In this embodiment, the stopper 128, tip shield 120 and label 142 are all formed of polymers wherein the relative energy distance Ra/Ro of such polymers relative to the cyclic olefin polymeric barrel 124 is greater than 0.75 to prevent adhesion of the stopper 128 and tip cap 130 to the barrel 124. Further, the use of a polymer for the label 142 having a relative energy distance Ra/Ro of such polymer relative to the cyclic olefin polymer barrel 124 greater than about 0.75 prevents stress cracking of the barrel at elevated temperatures. As will be understood, however, the label 142 may include a polymeric layer or polymeric adhesive in contact with the cyclic olefin barrel 124, wherein the outer layer is formed of a different material, including paper or foil. The method of forming the syringe assembly 120 may otherwise be identical to the method of forming the syringe assembly 20 described above.

Having described two preferred embodiments of the sterilizable transfer or storage device and method of this invention, it will be understood that various modifications may be made to the disclosed storage and transfer device and method of this invention within the purview of the appended claims. For example, the medical device of this invention may be a transfer set or vial wherein a first component is formed of a cyclic olefin polymer and a second component is formed from a second polymer, wherein the relative energy distance Ra/Ro of the second component relative to the cyclic olefin polymeric component is greater than 0.75 or more preferably equal to or greater than 1. As a further embodiment of the sterilizable transfer or storage device of this invention, a vial is formed of a cyclic olefin polymer and the stopper is formed of a second polymer, wherein the relative energy distance Ra/Ro of the second polymer selected for the stopper relative to the cyclic olefin polymeric vial is greater than 0.75 to prevent adhesion of the stopper to the vial and stress cracking of the vial at elevated temperatures, including autoclaving.

What is claimed is:

1. A sterilizable transfer or storage device for delivery or storage of a medicament, drug or vaccine, comprising a first member formed of a cyclic olefin polymer and a second member having a surface in contact with said first member formed of a second polymer, wherein the relative energy distance Ra/Ro of said second polymer relative to said cyclic olefin polymer is greater than 0.75 to prevent adhesion of said second member to said first member and stress cracking of said first member at elevated temperatures, including autoclaving.

2. The sterilizable transfer or storage device as defined in claim 1, wherein the molecular weight of said second member is at least 5,000.

3. The sterilizable transfer or storage device as defined in claim 1, wherein said first member is a syringe barrel and said second member is a plunger stopper.

4. The sterilizable transfer or storage device as defined in claim 3, wherein said plunger stopper is formed of a polymer selected from the group consisting essentially of styrene butadiene and a fluorocarbon polymer.

5. The sterilizable transfer or storage device as defined in claim 1, wherein said first member is a syringe barrel and said second member is a tip cap or tip shield in contact with said syringe barrel.

6. The sterilizable transfer or storage device as defined in claim 5, wherein said tip cap or tip shield having surface in contact with said syringe barrel formed of a styrene butadiene polymer.

7. A sterilizable syringe assembly including a generally tubular syringe body formed of a cyclic olefin polymer and a plunger having a stopper telescopically received in said syringe body in contact with an internal surface of said syringe body, said stopper formed of a second polymer wherein the relative energy distance Ra/Ro of said second polymer relative to said cyclic olefin polymer is greater than 0.75 to prevent adhesion of said stopper to said syringe body and stress cracking of said syringe body at the elevated sterilization temperature.

8. The sterilizable syringe assembly as defined in claim 6, wherein the relative energy distance Ra/Ro of said second polymer relative to said cyclic olefin is equal to or greater than one and the molecular weight of said second member is at least 5,000.

9. The sterilizable syringe assembly as defined in claim 7, wherein said plunger stopper is formed from a polymer selected from the group consisting essentially of styrene butadiene and a fluorocarbon polymer.

10. The sterilizable syringe assembly as defined in claim 7, wherein said syringe assembly further includes a tip cap or tip shield removably assembled on said syringe body, said tip cap or tip shield formed of a third polymer, wherein the relative energy distance Ra/Ro of said third polymer relative to said cyclic olefin polymer is greater than 0.7 to prevent adhesion of said tip cap or tip shield to said syringe body and stress cracking of said syringe body at elevated temperatures.

11. The sterilizable syringe assembly as defined in claim 10, wherein said third polymer is the same as said second polymer.

12. A method of making a sterilized syringe assembly comprising the following steps:

forming a generally tubular syringe barrel from a cyclic olefin polymer;

forming a plunger stopper from a second polymer, wherein the relative energy distance Ra/Ro of said second polymer relative to said cyclic olefin polymer of said syringe barrel is greater than 0.75;

telescopically receiving said plunger stopper in said generally tubular syringe barrel with said plunger stopper in contact with an inside surface of said generally tubular syringe barrel; and heating said syringe barrel and said plunger stopper to the sterilization temperature of said syringe barrel and plunger stopper.

13. The method of making a sterilized syringe assembly as defined in claim 12, wherein said method further includes forming a tip cap or tip shield from a third polymer, wherein the relative energy distance $Ra/Ro$ of said third polymer relative to said cyclic olefin polymer is greater than 0.75 and assembling said tip cap or tip shield on said syringe barrel before heating.

* * * * *